United States Patent [19]

Johnson et al.

[11] Patent Number: 4,840,786

[45] Date of Patent: Jun. 20, 1989

[54] AEROSOL ANTIPERSPIRANT COMPOSITIONS

[75] Inventors: Philip S. Johnson; Theresa A. Bakken, both of Cincinnati, Ohio

[73] Assignee: The Procter & Gamble Company, Cincinnati, Ohio

[21] Appl. No.: 171,618

[22] Filed: Mar. 22, 1988

[51] Int. Cl.$^4$ ............................................. A01N 25/02
[52] U.S. Cl. ........................................ 424/43; 424/46; 424/47; 424/68
[58] Field of Search ........................ 424/46, 47, 68, 43

[56] References Cited

U.S. PATENT DOCUMENTS

| | | | |
|---|---|---|---|
| 4,113,852 | 9/1978 | Kenkare | 424/46 |
| 4,278,655 | 7/1981 | Elmi | 424/47 |
| 4,359,456 | 11/1982 | Gosling | 424/68 |
| 4,411,883 | 10/1983 | Kenkare | 424/47 |

FOREIGN PATENT DOCUMENTS

| | | |
|---|---|---|
| 0028853 | 5/1981 | European Pat. Off. . |
| 28853 | 5/1981 | European Pat. Off. . |
| 183171 | 8/1986 | European Pat. Off. . |
| 191628 | 8/1986 | European Pat. Off. . |
| 1341618 | 12/1973 | United Kingdom . |
| 1341748 | 12/1973 | United Kingdom . |
| 2048229 | 12/1980 | United Kingdom . |
| 2144992 | 3/1985 | United Kingdom . |
| 8419734 | 3/1985 | United Kingdom . |

OTHER PUBLICATIONS

"Antiperspirants and Deodorants", Cosmetics, Science and Technology, vol. 2, pp. 373–416 (Balsam & Sagarin, Editors, 1972).
Ser. No. 171,619, filed 03/22/88 by Johnson & Bakken.

*Primary Examiner*—Thurman K. Page
*Assistant Examiner*—P. Prater
*Attorney, Agent, or Firm*—David K. Dabbiere; Douglas C. Mohl; Steven J. Goldstein

[57] ABSTRACT

An aerosol antiperspirant composition comprising:
(a) from about 2% to about 10% of a hydrophobic liquid;
(b) from about 20% to about 95% of a propellant;
(c) from about 2% to about 30% of an enhanced efficacy metallic antiperspirant material, containing at least about 30% of a high efficacy metallic species (by weight of all metallic species in said antiperspirant material);
(d) from about 0.1% to about 3.0% of a hydrophobically-treated hectorite clay;
(e) from about 0.1% to about 3% of a hydrophobically treated bentonite clay; and
(f) from about 0.01% to about 0.2% of an activator; wherein the level of said activator is less than $$0.03 + 0.165 \times \frac{(d)}{(d) + (e)}.$$

9 Claims, No Drawings

_4,840,786_

AEROSOL ANTIPERSPIRANT COMPOSITIONS

BACKGROUND OF THE INVENTION

This invention relates to aerosol antiperspirant compositions, and compositions for making them. More particularly, it relates to compositions having high efficacy and improved suspension stability.

Compositions designed to stop or reduce the flow of human perspiration are well known in the cosmetic and chemical literature. Antiperspirants typically contain an astringent material, such as an astringent aluminum or zirconium salt. The compositions are designed to deliver the active to the skin in an effective form; while being cosmetically acceptable.

Many antiperspirant compositions contain the antiperspirant active material in particulate form, suspended in an anhydrous liquid. These compositions are typicaly applied to the skin as sprays (both aerosols an non-pressurized pump sprays) and roll-ons. Many liquid formulations are described in S. Plechner, "Antiperspirants and Deodorants" 2 *Cosmetics, Science and Technology* 373-416 (M. Balsam and E. Sagarin, editors, 1972). Such compositions are also described, for example, in British Patent Specification No. 1,341,618, published Dec. 28, 1973; British Patent Specification No. 1,341,618, published Dec. 28, 1973; British Patent Specification No. 1,341,748, published Dec. 28, 1973; U.S. Pat. No. 4,278,655, Elmi, issued July 14, 1981; and European Patent Specification No. 28,853, Beckmeyer et. al., published June 20, 1981.

Antiperspirant compositions have also been described in the literature containing active materials with improved efficacy. These preferred actives have a selected distribution of polymeric aluminum metal species (containing aluminum with and without zirconium), resulting in improved antiperspirant efficacy. Such actives, and compositions containing them, are described, for example, in U.K. Patent application No. 2,048,229. Fitzgerald et al, published Dec. 10, 1980; U.S. Pat. No. 4,359,456, Gosling et al., issued Nov. 16, 1982; U.K patent application No. 2,144,992, Calalghan et al., published Mar. 20, 1985; European Patent Publication No. 183,171, Murray et al., published June 4, 1986; and European Patent Publcation No. 191,628, Inward et al., published Aug. 20, 1986.

It has been found that aerosal antiperspirant, containing preferred actives with suspension agents typically used in the art, may be subject to clogging. It has also been found that this clogging is particularly acute with preferred, high efficacy actives having selected polymeric distribution. Therefore, such compositions may be difficult or impossible to dispense from conventional aerosol containers.

It has now been found that the compositions of the present invention contain highly efficacious antiperspirant actives, with selected polymeric distribution, selected hydrophobically-treated clays and specific levels of activator (based on the clay levels) avoid this problem. Compositions of this invention also provide improved redispersibility (i.e., the ability to resuspend the antiperspirant active after settling.)

All percentages and ratios herein are by weight unless otherwise specified. Additionally all measurements are made at 25° C. unless otherwise specified.

SUMMARY OF THE INVENTION

This invention provides liquid antiperspirant suspensions comprising:

An aerosol antiperspirant composition comprising:
(a) from aoubt 2% to about 10% of a hydrophobic liquid;
(b) from about 20% to about 95% of a propellant;
(c) from about 2% to about 30% of an enhanced efficacy metallic antiperspirant material, continaig at least about 30% of a high efficacy metallic species (by weight of all metallic species in said antiperspirant material);
(d) from about 0.1% to about 3.0% of a hydrophobicallytreated hectorite clay;
(e) from about 0.1% to about 3.0% of a hydrophobicallytreated bentonite clay; and
(f) from about 0.01% to about 0.2% of an activator; wherein the level of said activator is less than $$0.03 + 0.165 \times \frac{(d)}{(d) + (e)}.$$

DESCRIPTION OF THE INVENTION

The antiperspirant compositions of this invention encompass as aerosol compositions intended for human use in order to deposit antiperspirant materials on human tissue. They may also contain certain optional components, such as, for example cosmetic powders, colorants, perfumes and emulsifiers. The essential and optional components included in these compositions must be "cosmetically acceptable", i.e., safe for human use and aesthetically acceptable at the levels encompassed by the present invention, at a reasonable risk/-benefit ratio.

In particular, these antiperspirant compositions comprise:

An aerosol antiperspirant composition comprising:
(a) from about 2% to about 10% of a hydrophobic liquid;
(b) from about 20% to about 95% of a propellant;
(c) from about 2% to about 30% of an enhanced efficacy metallic antiperspirant material, containing at least about 30% of a high efficacy metallic species (by weight of all metallic species in said antiperspirant material);
(d) from about 0.1% to about 3.0% of a hydrophobicallytreated hectorite clay;
(e) from about 0.1% to about 3% of a hydrophobicallytreated bentonite clay; and
(f) from about 0.01% to about 0.2% of an activator; wherein the level of said activator is less than $$0.03 + 0.165 \times \frac{(d)}{(d) + (e)}.$$

Preferably, the hydrophobic liquid carrier is present at a level of from about 4% to about 7%. The antiperspirant active material is preferably present at a level of from about 6% to about 12%. The hydrophobically treated hectorite clay is preferably present at a level from about 0.2% to about 0.88%. The hydrophobically treated bentonite clay is preferably present at a level from about 0.1 to about 0.4%. Preferably the activator is present at a level of from about 0.03% to about 0.2%, more preferably from about 0.04% to about 0.06%.

Preferably, the compositions of this invention are essentially free (i.e., containing less than about 1%) of free (not chemically-bound) water. Preferably, then, the antiperspiration active material and other material of this invention are dried so as to avoid introduction of water into the composition.

COMPONENTS

Hydrophobic Liquid Carrier:

The compositions of this invention contain a non-aqueous liquid (herein "hydrophobic liquid carrier") in which a particulate antiperspirant material is suspended. Such hydrophobic liquid carriers are well known in the art. Hydrophobic liquid carriers among those useful in this invention include fatty acid and fatty alcohol esters, water-insoluble ethers and alcohols, polyorgano silicones, and mixtures thereof. Such carriers are disclosed in the following patent documents, incorporated by reference herein: U.S. Pat. No. 4,053,851, Pader et al., issued Oct. 11, 1077; U.S. Pat. No. 4,065,564, Miles, Jr. et al., issued Dec. 27, 1977; U.S. Pat. No. 4,073,880, Pader et al, issued Feb. 14, 1978; U.S. Pat. No. 4,278,655, Elmi, issued July 14, 1981; and British patent application No. 2,018,590, Elmi et al., published Oct. 24, 1979.

Volatile silicone oils are preferred hydrophobic liquid carriers useful in the present compositions. (As used herein, "volatile" refers to those materials which have a measurable vapor pressure at ambient conditions). Such volatile silicone oils may be cyclic or linear. A description of various volatile silicone oils is found in Todd, et al., "Volatile Silicone Fluids for Cosmetics", 91 *Cosmetics and Toiletries*, 27-32 (1976), incorporated by reference herein. Preferred volatile silicone oils include those having from about 3 to about 9 silicon atoms, preferably containing from about 4 to about 5 silicon atoms. Cyclic volatile silicones useful herein include those of the following formula:

$$[\text{Si}(\text{CH}_3)_2-\text{O}]_n$$

wherein n=3 to 7. Linear volatile silicone oils include those of the formula:

$$(\text{CH}_3)_3\text{Si}-\text{O}-[\text{Si}(\text{CH}_3)_2-\text{O}]_n-\text{Si}(\text{CH}_3)$$

wherein n=1 to 7. Linear volatile silicones generally have viscosities of less than about 5 centisokes at 25° C., whereas the cyclic silicones have viscosities of less than about 10 centisokes. Examples of volatile silicone oils useful in the present invention include: Dow Corning 344, Dow Corning 345 and Dow Corning 200 (sold by Dow Corning Corporation); 7207 and 7158 (sold by General Electric Company); and SWS-03314 (sold by SWS Silicones Corporation).

Preferably the present compositions contain from about 0.2% to about 7% of one or more liquid emollients as part of the hydrophobic liquid carrier. These emollients can be either a nonvolatile silicone or a liquid paraffin material such as mineral oil. Such materials have a viscosity of from about 5 to about 2,500,000 centistokes, preferably from about 10 to about 100,000 centistokes, at 25° C. Preferably, the non-volatile emollient is a silicone fluid, such as a polyalkyl siloxane, a polyalkylaryl siloxane, or a polyether siloxane copolymer.

The essentially non-volatile polyalkyl siloxanes useful herein include, for example, polydimethyl siloxane with viscosities of from about 5 to about 100,000 centistokes at 25° C. Such polyalkyl siloxanes include the Vicasil series (sold by General Electric Company) and the Dow Corning 200 series (sold by Dow Corning Corporation). Polyalkylarl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolyemrs are preferred copolymers for use in the present compositions.

Enhanced Efficacy Antiperspirant Active:

The present compositions contain a particulate metallic antiperspirant material (herein an "enhanced efficacy metallic antiperspirant material", containing at least about 30% of a high efficacy metallic species (by weight of all metallic species in said antiperspirant material). The enhanced efficacy metallic antiperspirant materials include the inorganic and organic salts of aluminum, zirconium and mixtures thereof.

Particularly preferred are the aluminum and zirconium salts such as aluminum halides, aluminum hydroxide halide, zirconyl oxide halides, zirconyl hydroxy halides, and mixtures thereof. Preferred aluminum salts include those of the formula $$\text{Al}_2(\text{OH})_a\text{Cl}_b \cdot x\text{H}_2\text{O}$$

wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5, and "2/3 basic chlorhydroxide," wherein a=4. Processes for preparing aluminum salts are disclosed in the following documents, all incorporated by reference herein: U.S. Pat. No. 3,887,692, Gilman, issued June 3, 1975; U.S. Pat. No. 3,904.741, Jones et al., issued Sept. 9, 1975; U.S. Pat. No. 4,359,456, Gosling, et al., issued Nov. 16, 1982; and British Patent Specification No. 2,048,229, Fitzgerald, et al., published Dec. 10, 1980. Mixtures of aluminum salts are described in British Patent Specification No. 1,347,950, Shin, et al., published Feb. 27, 1974 (incorporated by reference herein).

Zirconium salts are also preferred for use in antiperspirant compositions of the present invention. Such salts are of the general formula $$\text{ZrO}(\text{OH})_{2-a}\text{Cl}_a \cdot x\text{H}_2\text{O}$$

wherein a is from about 1.5 to about 1.87; x is from about 1 to about 7; and wherein a and n may have non-integer values. These circonium salts are disclosed in Belgium Pat. No. 825,146, Schmitz, published Aug. 4, 1975, (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in U.S. Pat. No. 3,679,068, Luedders, et al., issued Feb. 12, 1974 (incorporated herein by reference), and U.S. Pat. No. 4,120,948, Shelton, issued Oct. 17, 1978 (incorporated by reference herein).

These metallic astringent salts are comprised of a mixture of metallic species, i.e., containing metallic ratios of different valences. As described in the literature, the antiperspirant efficacy of these species may vary. In particular, specific aluminum-containing species (herein, a "preferred metallic species") have been found to have enhanced antiperspirant efficacy in aluminum chlorhydrate and zirconium-aluminum complexed actives. The enhanced efficacy metal antiperspirant actives of this invention contain at least about 30% (by weight of all metal-containng species) of such preferred antiperspirant species.

"Enhanced efficacy aluminum chlorhydrates" among those useful herein are desribed in the following patent documents, all incorporated by reference herein: U.K. patent application No. 2,048,229 Fitzgerald et al., published Dec. 10, 1980; U.S. Pat. No. 4,359,456, Gosling et al., issued Nov. 16, 1982; European patent application No. 183,171, Murray et al., published June 4, 1986; and European patent application No. 191,628, Inward et al., published Aug. 29, 1986. These enhanced efficacy aluminum chlorhydrate materials contain a preferred metallic species that is the third aluminum fraction isolated (or detected) in size exclusion chromatography of the aluminum chlorhydrate material. This species is described as the "Band III" species in U.S. Pat. No. 4,359,456, incorporated herein by reference. Chromatographic methods useful in identifying such aluminum-containing species are also described in the '456 Patent.

The enhanced efficacy aluminum chlorhydrates of the present compositions contain at least about 30%, preferably at least about 40% (by weight of all aluminum species in said material), of the preferred metallic species. Also preferably, the enhanced efficacy aluminum chlorhydrates of this invention contain less than about 20%, more preferably less than about 10%, more preferably less than about 1% (by weight of all aluminum species in said material), of the first aluminum fraction isolated in size exclusion chromatography of the aluminum chlorhydrate material.

Enhanced efficacy zirconium-aluminum complex actives among those useful in this invention are described in U.K. patent application No. 2,144,992, Callaghan et al., published August 16, 1983. Size exclusion chromatography of these enhanced efficacy aluminum-zirconium actives typically yields five metal containing species. The enhanced efficacy zirconium-aluminum actives of this invention contain at least about 30% (by weight of all metal species in said material) of the fourth metallic species isolated by size exclusion chromatography of said material.

Hydrohobically-treated Hectorite Clay:

The compositions of this invention contain selected hydrophobically-treated hectorite clays as suspension agents. Many such hectorite clays are commercially available. They include, for example, Bentone 38 sold by NL Industries, Inc.

Hydrophobically-treated Bentonite Clay:

The compositions of the present invention also contain selected hydrophobically-treated bentonite clays. Such bentonite clays useful in the present invention include, for example, Bentone 34, sold by NL Industries, Inc., and Tixogel VP sold by United Catalyst, Inc.

The hectorite and bentonite clay minerals of the instant compositions can be described as expandable (swellable), threelayer layer calys, in which a sheet of aluminum/oxygen atoms or magnesium/oxygen atoms lies between two layers of silicone/oxygen atoms, i.e., aluminosilicates and magnesium silicates, having an ion exchange capacity of at least about 50 meq/100 g. of clay, and preferably at least about 60 meq/100 g. of clay. The term "expandable" as used to describe clays relates to the ability of the layered clay structure to be swollen or expanded on contact with water. Such hectorite and bentonite clays are described in Grim, *Clay Mineralogy* (2nd. Ed.) pp. 77–79 (1968), and in Van Olphen, *An Introduction to Clay colloid Chemistry*, (2nd Ed.) pp 64–76 (1977), both of which are incorporated by reference herein.

The clay minerals employed in the compositions of the instant invention contain exchangeable cations including, but not limited to, protons, sodium ions, potassium ions, calcium ions, magnesium ions, lithium ions, and the like.

It is customary to distinguish between clays on the basis of one cation predominantly or exclusively absorbed, For example, a sodium clay is one in which the absorbed cation is predominantly sodium. As used herein, the term clay, such as a hectorite clay, includes all the various exchangeable cation variants of that clay, e.g. sodium hectorite, potassium hectorite, lithium hectorite, magnesium hectorite, calcium hectorite, etc.

The clay minerals employed in the compositions of the instant invention are made hydrophobic by treating them with a cationic surfactant material. A preferred cationic surfactant is a quaternary ammonium cationic surfactant. A particularly preferred cationic surfactant is ditallow dimethyl ammonium chloride (e.g., quaternium-18).

Suspension Agent Activator:

The compositions of this invention contain an "activator" for the hectorite and bentonite clays that enables the hydrophobically-treated clays of this invention to suspend the antiperspirant active in the hydrophobic liquid carrier. Many such activators are known in the art. Such activating materials include, for example, propylene carbonate, ethanol, and mixtures thereof.

The level of this activator is less than the amount defined in the following equation:

$$0.03 + 0.165 \times \frac{\text{level of bentonite clay}}{\text{level of bentonite clay} + \text{level of hectorite clay}}$$

Without being limited by theory, it is believed that this level of activator will activate the clay without causing bridging between particles of active and particles of clay forming agglomerates that can lodge in the valve.

Optional Components:

The compositions of the present invention may also contain optional components that modify the physical characteristics of the vehicles or serve as "active" components when deposited on the skin in addition to the particulate antiperspirant material. Additional active components include bacteriostats and fungistats. Optional components useful herein are described in the following patent documents, all incorporated by reference herein. U.S. Pat. No. 4,049,792, Elsnau, issued Sept. 20, 1977; and European Patent Specification No. 28,853, Beckmeyer, et al., published June 20, 1981. The particular non-active components that may be useful will depend upon the form of application that is desired. Such components include, for example, emollients, colorants, perfumes, and emulsifiers.

Methods

The compositions of this invention may be made by a variety of methods well known in the art. The specific methods employed may vary, of course, according to the particular components used. A preferred method for making aerosol compositions of this invention, for delivery from a suitable aerosol container, comprises the steps of:

(a) preparing a concentrate by mixing and milling the hydrophobic liquid carrier, the hectorite and bentonite clays, and activator; and adding the enhanced efficacy antiperspirant material to the mixture either before or after milling;

(b) filling the concentrate into the container; and (c) pressurizing the container by adding a propellant into the container and sealing the container.

The following non-limiting examples illustrate the compositions, processes and uses of the presesnt invention.

EXAMPLE I

An antiperspirant aerosol of this invention is made comprising:

| Component | % (by weight) |
|---|---|
| Cyclomethicone | 7.04 |
| Dimethicone | 1.00 |
| Isopropyl myristate | 0.50 |
| Westwood DM200[1] | 9.00 |
| Tixogel VP | 0.34 |
| Bentone 38 | 0.22 |
| Propylene carbonate | 0.07 |
| Fragrance | 0.20 |
| A-46 propellant[2] | 81.60 |

[1] enhanced efficacy aluminum chlorhydrate manufactured by Westwood Chemical Corporation, having approximately 40% (by weight of aluminum species) of preferred metallic species (Band III aluminum-containing chromatographic species) and approximately 0% of Band I aluminum-containing chromatographic species
[2] volatile propellant, mixture of 87% isobutane and 13% propane (by weight of total propellant)

An antiperspirant aerosol is made by admixing the concentrate components. The concentrate, including active, is milled under high sheer conditions. The concentrate components are added to a standard aerosol can. The propellant and fragrance are then added, under pressure, and the can sealed.

The product, when applied to the underarm are of a human subject, is effective as an antiperspirant.

EXAMPLE II

| Component | % (by weight) |
|---|---|
| Cyclomethicone | 5.3 |
| Dimethicone | 0.5 |
| Isopropyl palmitate | 2.0 |
| Wicken-APO-30[1] | 9.0 |
| Bentone-38 | 0.5 |
| Tixogel-VP | 0.2 |
| Propylene carbonate | 0.05 |
| A-31 propellant[2] | 82.45 |

[1] enhanced efficacy Aluminum Chlorhydrate sold by Wicken Chemical division of Dow Corning
[2] mixture of 96% isobutane and 3% n-butane An antiperspirant aerosol is made by combining the components as described above in Example 1.

The product, when applied to the underarm of a human subject, is effective as an antiperspirant.

What is claimed is:

1. An aerosol antiperspirant composition comprising:
   (a) from about 2% to about 10% of a hydrophobic liquid selected from the group consisting of fatty acid and fatty alcohol esters, water-insoluble ethers and alcohols, polyorganosilicones, and mixtures thereof;
   (b) from about 20% to about 95% of the propellant;
   (c) from about 2% to about 30% of an enhanced efficacy metallic antiperspirant material, containing at least about 30% of a high efficacy metallic species (by weight of all metallic species in said antiperspirant material);
   (d) from about 0.1% to about 3.0% of a hydrophobically-treated hectorite clay;
   (e) from about 0.1% to about 3.0% of a hydrophobically-treated bentonite clay; and
   (f) from about 0.01% to about 0.2% of an activator selected from the group consisting of propylene carbonate, ethanol, and mixtures thereof;
wherein the level of said activator is less than $$0.03 + 0.165 \times \frac{(d)}{(d) + (e)}.$$

2. An antiperspirant composition according to claim 1, wherein said activator is propylene carbonate.

3. An antiperspirant composition according to claim 1, wherein said activator is present at a level of from about 0.04% to about 0.06%.

4. An antiperspirant composition according to claim 2, wherein said enhanced efficacy metallic antiperspirant material is an enhanced efficacy aluminum chlorhydrate.

5. An antiperspirant composition according to claim 4, wherein said enhanced efficacy aluminum chlorhydrate least about 40% (by weight of all aluminum species in said aluminum chlorhydrate) of the preferred metallic species.

6. An antiperspirant composition according to claim 5, wherein said enhanced efficacy aluminum chlorhydrate contains less than about 1% (by weight of all aluminum species in said aluminum chlorhydrate) of the first aluminum fraction isolated in size exclusion chromatography of said aluminum chlorhydrate.

7. An antiperspirant composition according to claim 2, wherein said enhanced efficacy aluminum chlorhydrate is an enhanced efficacy zirconium-aluminum complex.

8. An antiperspirant suspension composition according to claim 2, wherein said hydrophobic liquid carrier comprises a polyorgano silicone.

9. A method for making an aerosol antiperspirant composition according to claim 1, for delivery from a suitable aerosol container, comprising the steps of:
   (a) preparing a concentrate by mixing and milling said hydrophobic liquid carrier, said activator and said hectorite and bentonite clays; and adding said enhanced efficacy antiperspirant material to the mixture of said materials either before or after said milling;
   (b) filling said concentrate into said container; and
   (c) pressurizing said container by adding said suitable aerosol propellant into said container and sealing said container.

* * * * *

UNITED STATES PATENT AND TRADEMARK OFFICE
CERTIFICATE OF CORRECTION

PATENT NO. : 4,840,786

DATED : June 20, 1989

INVENTOR(S) : Philip S. Johnson and Theresa A. Bakken

It is certified that error appears in the above-identified patent and that said Letters Patent is hereby corrected as shown below:

Column 2, line 64 "0.88%" should read -- 0.8% -- .

Signed and Sealed this

Twenty-fourth Day of September, 1991

Attest:

HARRY F. MANBECK, JR.

Attesting Officer

Commissioner of Patents and Trademarks